United States Patent [19]

Tchao

[11] Patent Number: 5,601,997
[45] Date of Patent: Feb. 11, 1997

[54] CHEMOTAXIS ASSAY PROCEDURE

[76] Inventor: Ruy Tchao, Philadelphia College of Pharmacy and Science, 600 S. 43rd St., Philadelphia, Pa. 19104

[21] Appl. No.: 383,058

[22] Filed: Feb. 3, 1995

[51] Int. Cl.⁶ ....................... C12Q 1/02
[52] U.S. Cl. ................... 435/29; 435/34
[58] Field of Search .............. 435/29, 34, 30, 435/285, 300, 301; 422/101

[56] References Cited

U.S. PATENT DOCUMENTS

| | | | |
|---|---|---|---|
| 4,912,037 | 3/1990 | Guirguis et al. | 435/285 |
| 5,210,021 | 5/1993 | Goodwin, Jr. | 435/29 |
| 5,284,753 | 2/1994 | Goodwin, Jr. | 435/30 |
| 5,302,515 | 4/1994 | Goodwin, Jr. | 435/29 |

FOREIGN PATENT DOCUMENTS 1581766  12/1980  United Kingdom .

OTHER PUBLICATIONS

Stephen Boyden, Ph.D., "The Chemotactic Effect of Mixtures of Antibody and Antigen on Polymorphonuclear Leucocytes" *J. Exp. Med.* 115: pp. 453–466, (1962).
Zichia et al., A New Direct Viewing Chemotaxis Chamber, Journal of Cell Science 99, 769–775 (1991).
Wilkinson, Micropore Filter Methods for Leukocyte Chemotaxis, Methods in Enzymology 162, 38–50 (1988).
NeuroProbe MB Series Microtiter Plate Chambers, NeuroProbe, Inc. (1994).

*Primary Examiner*—Leslie Wong
*Attorney, Agent, or Firm*—Panitch Schwarze Jacobs & Nadel, P.C.

[57] ABSTRACT

A chemotaxis assay procedure which is non-destructive of the cells being studied, which permits the ready performance of kinetic or time-dependent study of cell migration from the same sample, and which produces objective measurements includes the steps of: (a) labeling cells with a dye; (b) placing the labeled cells in a first chamber; (c) placing a chemical agent in a second chamber adjacent to said first chamber; (d) separating said first chamber from said second chamber with a radiation opaque membrane, said radiation opaque membrane having a plurality of substantially perpendicular transverse pores therein; (e) stimulating the labeled cells on the side of the membrane closest to said second chamber with electromagnetic radiation of a first wavelength whereby said labeled cells will emit electromagnetic radiation of a second wavelength; and (f) measuring the emitted electromagnetic radiation from the side of the radiation opaque membrane closest to the second chamber; wherein said radiation opaque membrane comprises a film which is not substantially transmissive to at least one of said first and second wavelengths of electromagnetic radiation. The radiation opaque membrane may comprise a dyed film or a film which has at least one radiation blocking layer applied thereto.

15 Claims, 7 Drawing Sheets

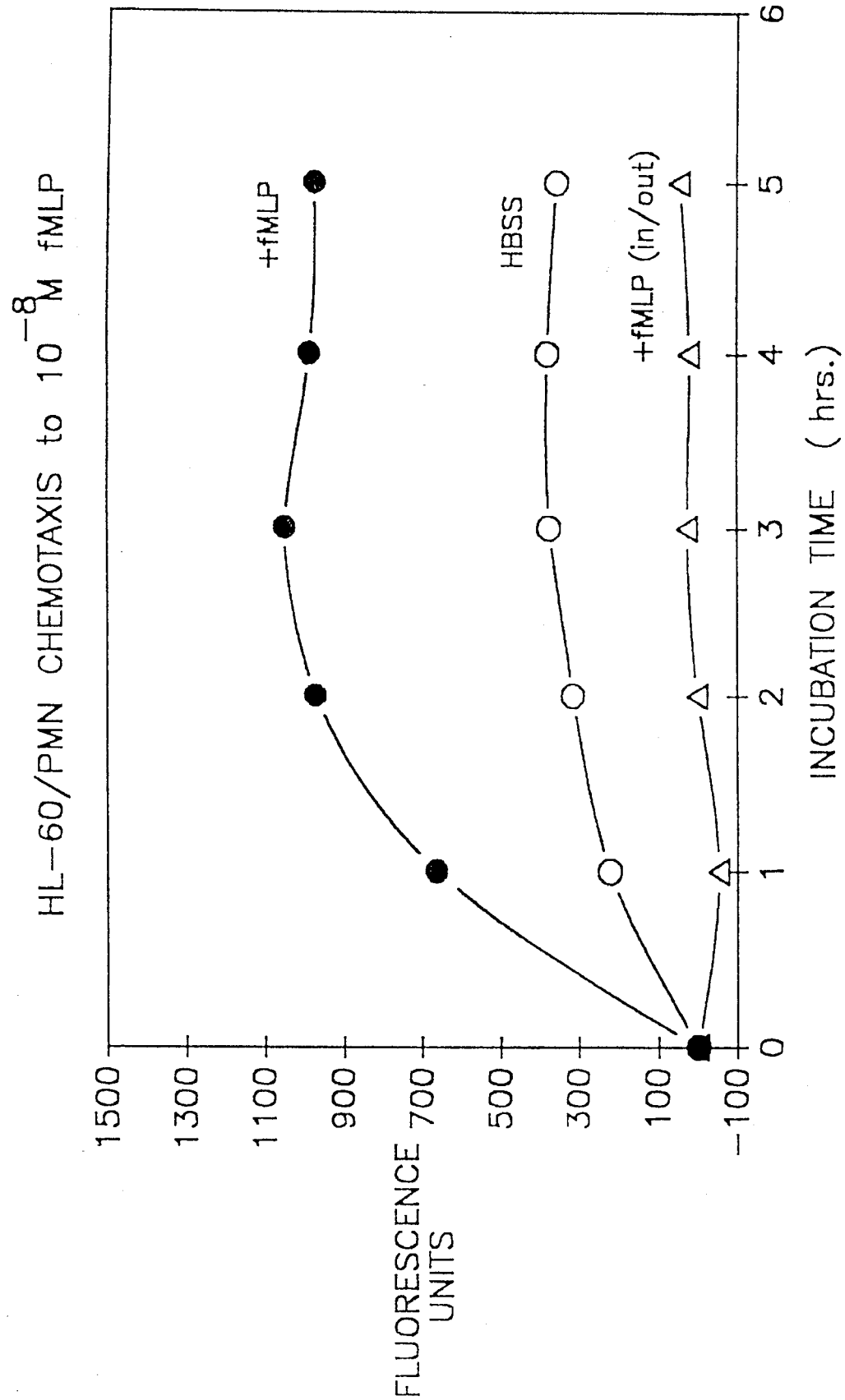

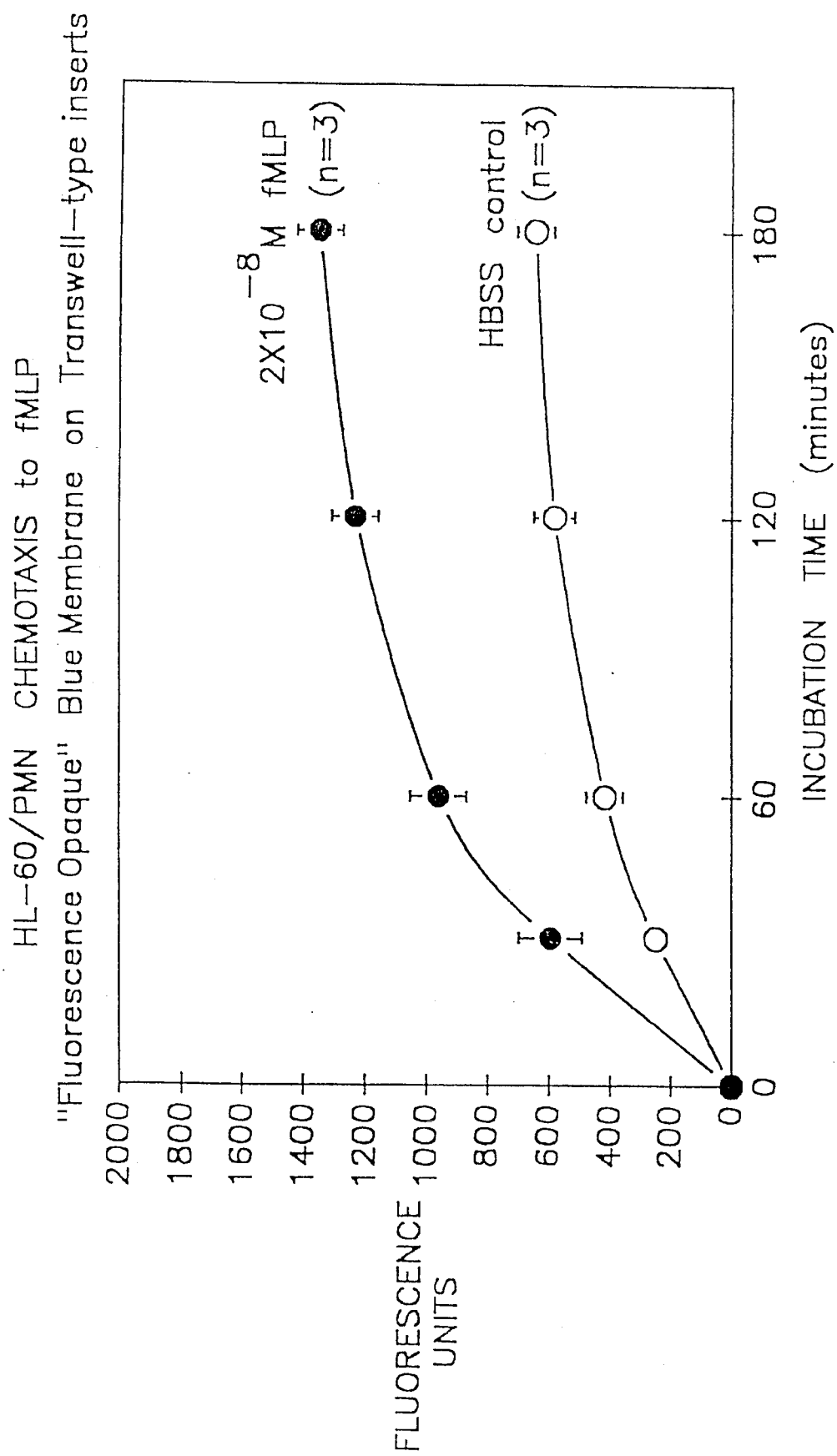

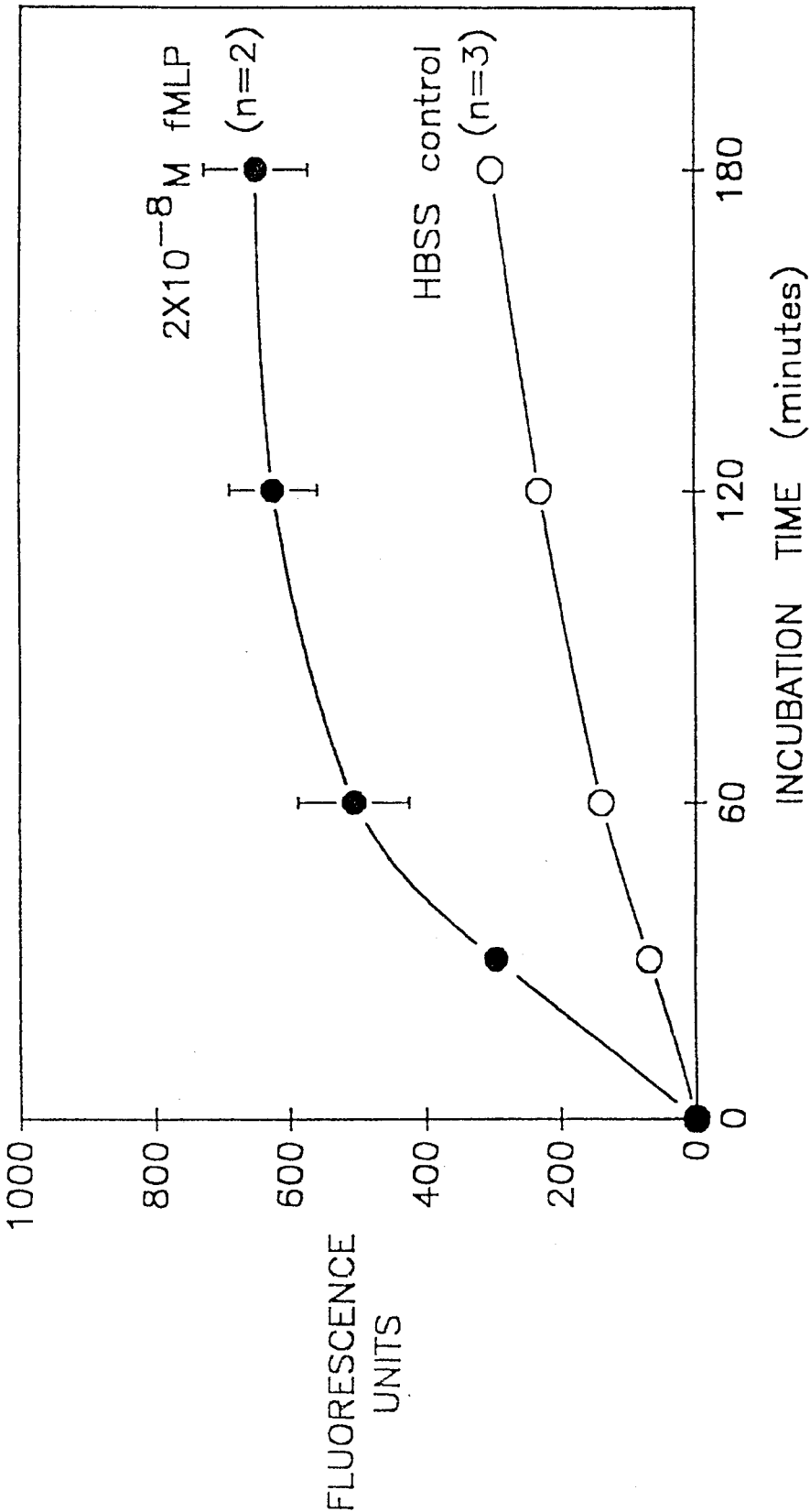

CHEMOTAXIS ASSAY PROCEDURE

FIELD OF THE INVENTION

This invention relates to a chemotaxis assay procedure and, more particularly, relates to an in vitro chemotaxis assay procedure which is non-destructive of the cell sample and permits kinetic study of the chemotactic response. This invention also relates to a novel radiation opaque membrane for use in the chemotaxis procedure.

BACKGROUND OF THE INVENTION

Chemotaxis is broadly defined as the orientation or movement of an organism or cell in relation to a chemical agent. Chemotaxis assays, particularly in vitro chemotaxis assays, are widely used procedures in medical, biological, pharmaceutical and toxicological research. Such assays are perhaps most widely used to determine the effect of a chemical agent on the inflammatory process, either as a stimulant or inhibitor of that process.

The currently used chemotaxis assay procedure derives from that originally developed by S. Boyden in 1962. (See, S. Boyden, *The Chemotactic Effect of Mixtures of Antibody and Antigen on Polymorphonuclear Leucocytes*, J. Exp. Med. 115: pp. 453–466, 1962). Essentially, the procedure involves placing a suspension of neutrophils and a chemical agent in two separate chambers, which chambers are separated by a polycarbonate filter. The neutrophils are typically either human polymorphonuclear neutrophils ("PMN's") prepared from the peripheral blood of volunteers or PMN's prepared from the peritoneal fluid of animals, such as guinea pigs or rabbits.

After a predetermined period of time, the filter is removed and cells on the filter surface closest to the chamber containing the cell suspension are carefully removed. The remaining cells on the filter are then fixed and stained. Using a high power microscope, the filter is examined and the number of cells appearing on the underside of the filter (i.e., the side of the filter closest to the chamber containing the chemical agent) are counted manually. A positive chemotactic response is indicated by the cells having migrated or "crawled" through the filter to the side closest to the chamber containing the chemical agent. Because of the time required to do so, typically the entire filter is not examined. Rather, representative sample areas are examined and counted.

There are several disadvantages to this procedure. The examination and counting of the cells on the filter is time-consuming, tedious and expensive. It is also highly subjective because it necessarily involves the exercise of judgment in determining whether to count a cell that has only partially migrated across the filter. In addition, the time and expense associated with examining the entire filter necessitates that only representative areas, selected at random, be counted, thus rendering the results less accurate than would otherwise be the case if the entire filter were examined and counted.

Perhaps the most important disadvantage in this procedure is that the fixing step kills the cells. That is, the procedure is destructive of the cell sample. Thus, in order to determine a time-dependent relationship of the chemotactic response; that is, a kinetic study, of a particular chemical agent, it is necessary to run multiple samples for each of multiple time periods. When one considers that multiple samples, as well as positive and negative controls, are necessary to obtain reliable data, a single chemotaxis assay can produce dozens of filters, each of which needs to be individually examined and counted. The time and expense associated with a time-dependent study is usually prohibitive of conducting such a study using the Boyden procedure.

Alternatives to the Boyden assay have been proposed to overcome some of the above disadvantages. See generally, P. Wilkinson, *Micropore Filter Methods for Leukocyte Chemotaxis*, Methods in Enzymology, Vol. 162, (Academic Press, Inc. 1988), pp. 38–50. See also, Goodwin, U.S. Pat. No. 5,302,515; Guiruis et al., U.S. Pat. No. 4,912,057; Goodwin, U.S. Pat. No. 5,284,753; and Goodwin, U.S. Pat. No. 5,210,021. Although the chemotaxis devices and procedures described in these references have some advantages over the original Boyden procedure and apparatus, they are not without their shortcomings. For example, all of these procedures, like Boyden, require that the filter be removed and the non-migrated cells wiped or brushed from the filter before the migrated cells can be counted. In addition, most of these procedures require fixing and staining the cells and none of them permit the kinetic or time-dependent study of the chemotactic response of the same cell sample.

SUMMARY OF THE INVENTION

I have developed a chemotaxis assay procedure which avoids the above disadvantages, which is non-destructive, and which readily permits kinetic study of the chemotactic response. The chemotaxis procedure of this invention is simple, quick and inexpensive to perform, produces objective data, and is usable with a variety of different cell types.

Basically, the non-destructive chemotaxis assay procedure comprises the steps of;

a) labeling cells with a dye;

b) placing the labeled cells in a first chamber;

c) placing a chemical agent in a second chamber adjacent to said first chamber;

d) separating said first chamber from said second chamber with a radiation opaque membrane, said radiation opaque membrane having a plurality of substantially perpendicular transverse pores therein;

e) stimulating the labeled cells on the side of the membrane closest to said second chamber with electromagnetic radiation of a first wavelength whereby said labeled cells will emit electromagnetic radiation of a second wavelength; and f) measuring the emitted electromagnetic radiation from the side of the radiation opaque membrane closest to the second chamber; wherein said radiation opaque membrane comprises a film which is not substantially transmissive to at least one of said first and second wavelengths of electromagnetic radiation.

In another aspect, the invention comprises a radiation opaque membrane for use in a chemotaxis assay procedure wherein cells labeled with a dye are stimulated with electromagnetic radiation of a first wavelength whereby the cells will emit electromagnetic radiation of a second wavelength, said radiation opaque membrane comprising a film which is not substantially transmissive to at least one of said first or second wavelengths of electromagnetic radiation, said radiation opaque membrane having a plurality of substantially perpendicular transverse pores therein.

These and other aspects of the invention will become apparent upon a reading of the following detailed description of the embodiments, with reference to the drawings, and the appended claims.

BRIEF DESCRIPTION OF THE DRAWINGS

FIGS. 4–7 are graphs of fluorescence units vs. incubation time of the chemotaxis data generated by the Examples.

DETAILED DESCRIPTION OF THE EMBODIMENTS

Although not critical to the present invention, a description of the preferred apparatus for use in carrying out the chemotaxis procedure of this invention is included because it is believed to be helpful in illustrating the advantages of this invention over the prior art. It is to be expressly understood, however, that any number of devices may be used in carrying out the present procedure and the invention is not limited to the use of any particular apparatus, except as set forth in the appended claims.

Figure 1:
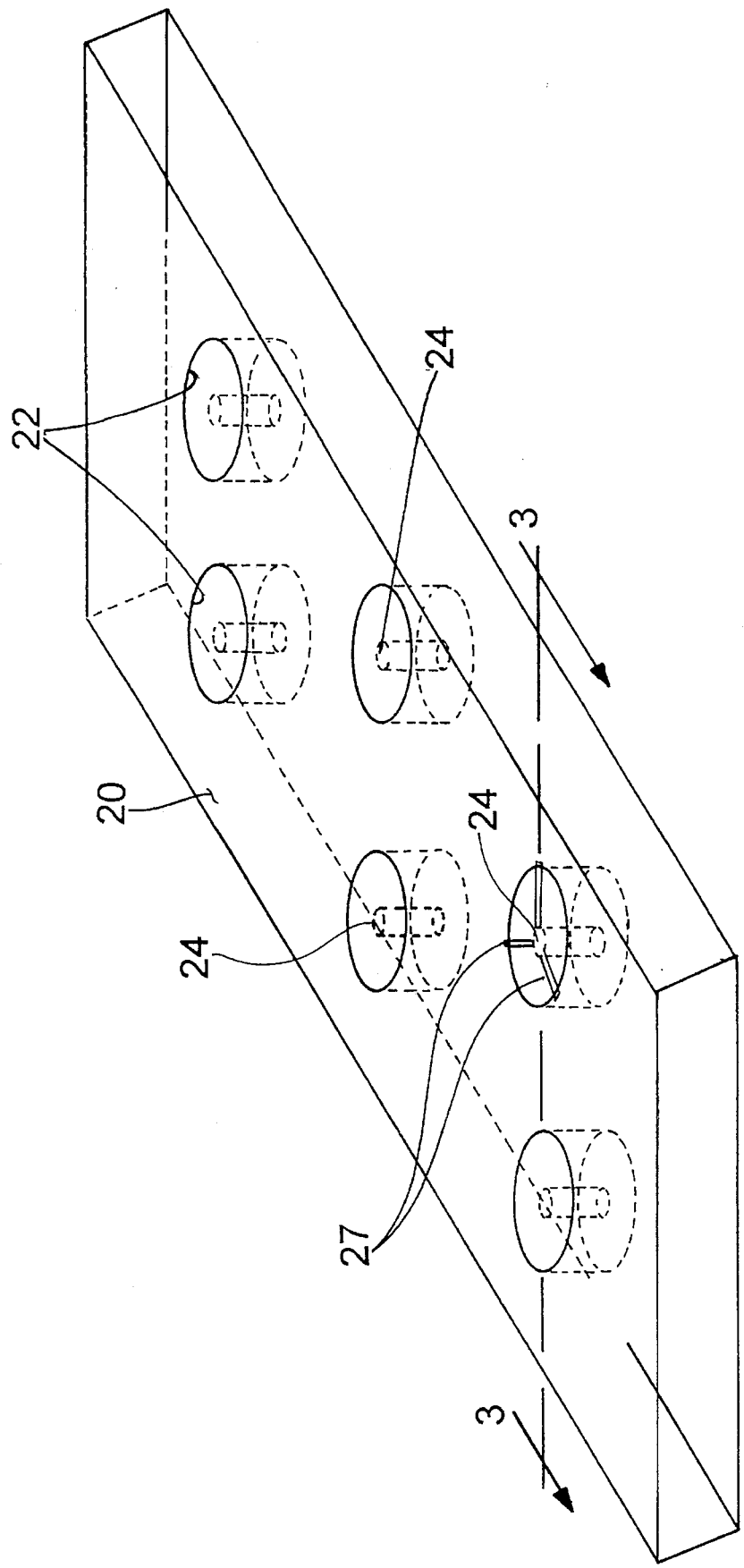
FIG. 1 is a perspective view of a preferred apparatus used in carrying out the present procedure.
Figure 2:
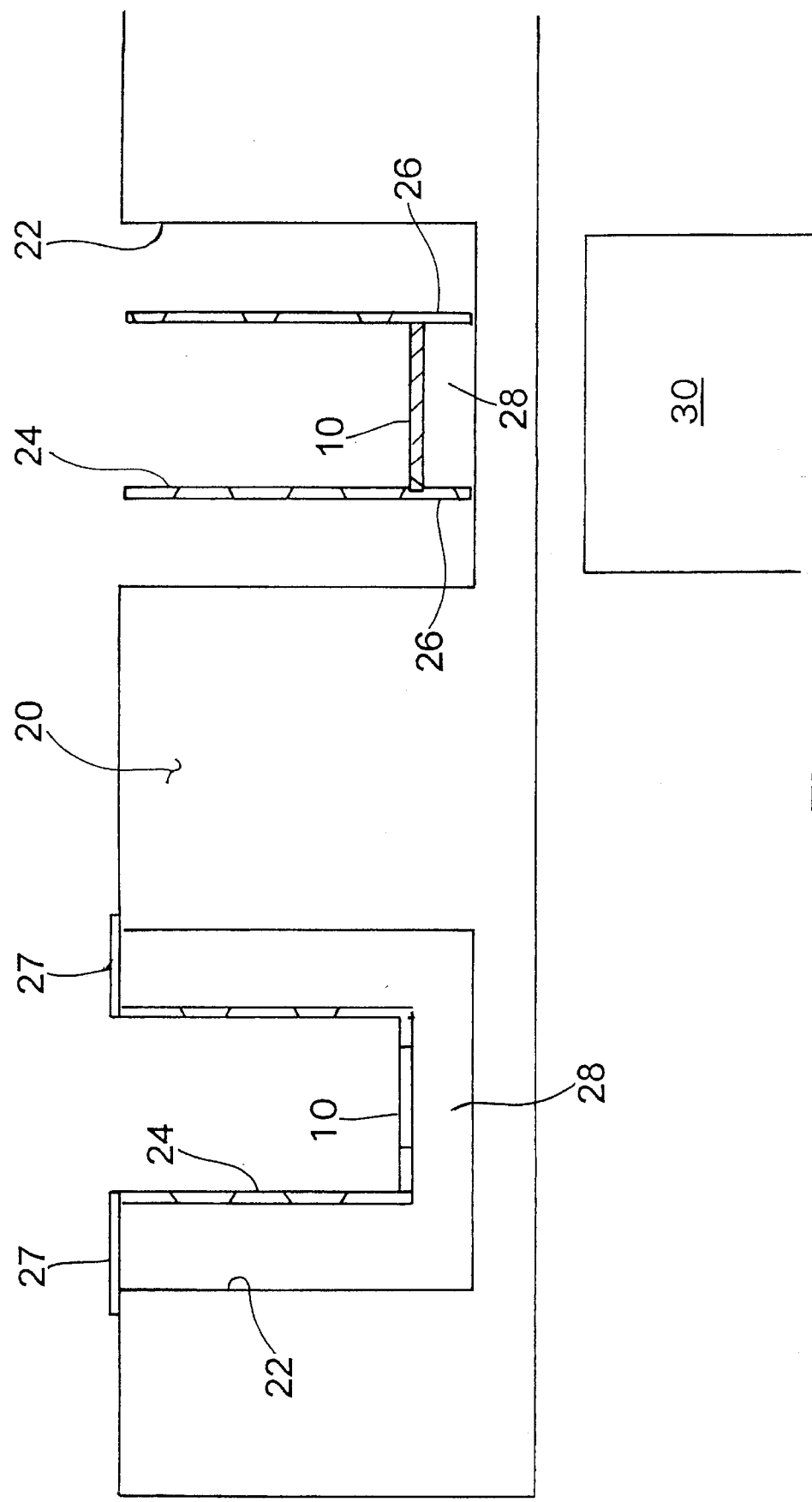
FIG. 2 is an enlarged, sectioned view of the apparatus of FIG. 1 as seen along line 2—2 of FIG. 1.

With reference first being made to FIGS. 1 and 2, the preferred apparatus comprises a multi-well culture plate which is widely available from a variety of commercial sources. This type of apparatus is commonly employed to study the effects of chemical agents on cell growth. As seen in FIGS. 1 and 2, the apparatus comprises a plate 20 having a plurality of spaced-apart wells 22. Each well 22 is provided with an insert 24 adapted to fit inside the well. In the parlance of this specification, the interior of the insert comprises one chamber and the exterior of the insert comprises a second chamber. The size, shape and number of wells 22, inserts 24, and plate 20 are not critical to this invention.

Figure 3A:
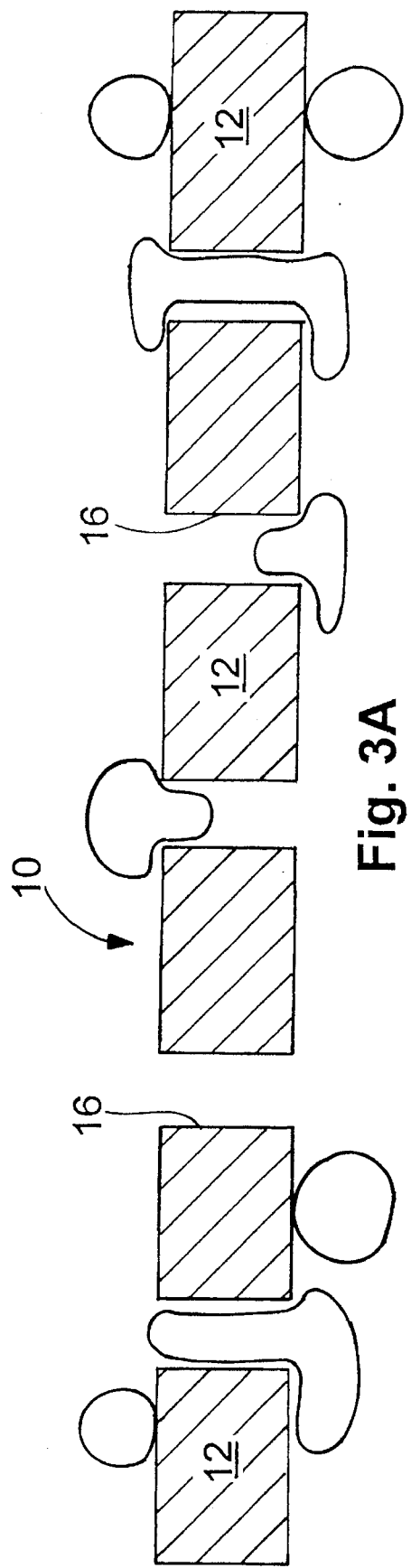
FIG. 3A is a simplified schematic view, in cross-section, of cells migrating across one embodiment of the radiation opaque membrane of the present invention.
Figure 3B:
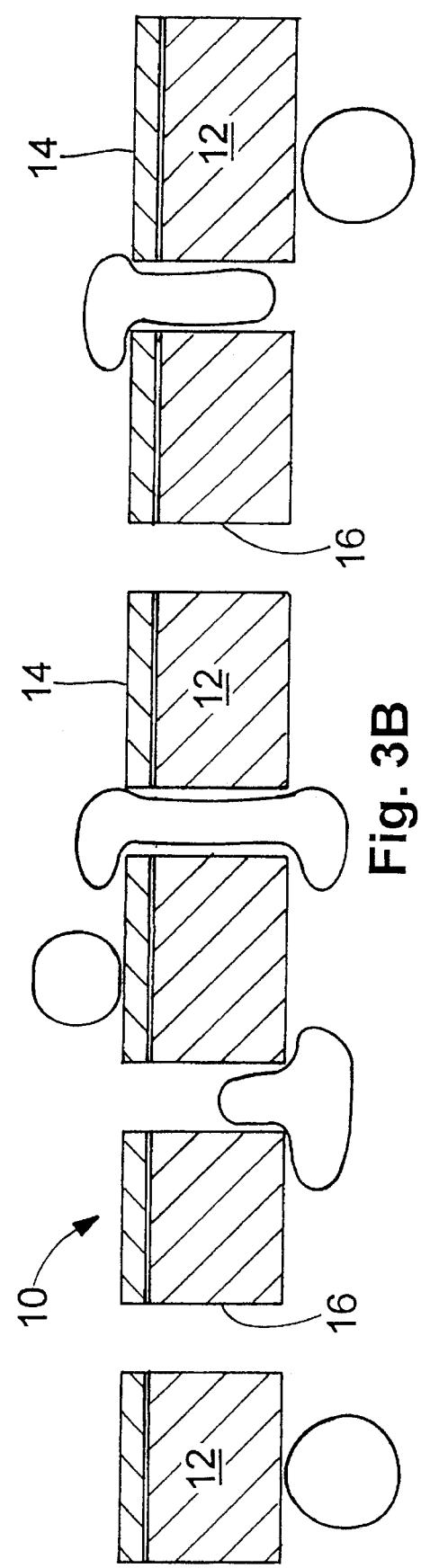
FIG. 3B is a simplified schematic view, in cross-section, of cells migrating across another embodiment of the radiation opaque membrane of the present invention.

For purposes of this invention, the bottom of the insert 24 has been provided with a radiation opaque membrane 10 of this invention, which separates the two chambers. The radiation opaque membrane 10 may be attached to the bottom of the insert by any conventional means, such as glue or other adhesive, heat welding, ultrasonic welding, etc. In practice, the labeled cells are placed in the insert 24 and the chemical agent is placed in the well 22. The chemotactic reaction will cause the labeled cells to migrate or "crawl" from the chamber 24 to chamber 22, through the pores 16 in the radiation opaque membrane 10, as particularly shown in FIGS. 3A and 3B.

As seen in FIG. 2, a space 28 is created between the radiation opaque membrane 10 and the bottom of the well 22. A distance of about 1 mm between the bottom of well 22 and the radiation opaque membrane 10 is generally sufficient to permit the free migration of cells across the radiation opaque membrane. The space 28 may be conveniently created by providing the insert 24 with stand-offs 26, which may take any convenient form or shape (e.g. legs, bosses, flange, etc.). When using stand-offs, care should be taken not to isolate the fluid in space 28 from the remainder of the fluid in the well 22, which would tend to create a separate concentration gradient in the space 28. Alternatively, the space 28 may be created by suspending the insert 24 within the well 22 by the use of, for example, radial projections 27 which rest on the surface of plate 20 as shown in FIGS. 1 and 2.

At predetermined periods, the quantum of cells that have migrated across the radiation opaque membrane will be determined by first exciting or stimulating the labeled cells on the side of the radiation opaque membrane 10 closest to the chamber 22 and measuring the radiation emitted by those labeled cells. With the preferred apparatus illustrated in FIGS. 1 and 2, this step would comprise stimulating and measuring the radiation from below the radiation opaque membrane 10, that is, through space 28. It will be understood by those skilled in the art that it is preferred that at least the chamber through which the stimulation and measurement of radiation will take place is substantially transparent to both the radiation being measured and any radiation needed to excite or stimulate the dye used to label the cells. In the preferred embodiment, the apparatus is made of a clear, transparent material, such as polystyrene, polycarbonate, LUCITE®, glass, etc.

The device 30 used to stimulate the cells and measure the emitted radiation will, of course, depend on the dye used to label the cells and the type of apparatus used for the assay procedure. For example, if the plate apparatus of FIGS. 1 and 2 is used, a fluorescent plate reader, such as a Cytofiuor™ 2300 (Millipore Corp., Marlborough, MA), can be used to advantage. The radiation opaque membrane 10 will substantially prevent either the stimulation of the cells in chamber 24 or the transmission of radiation from the cell sample in chamber 24 into the space 28, or will prevent both. Accordingly, the radiation measured will provide a direct quantitative measure of the number of cells that have migrated across the radiation opaque membrane 10 from chamber 24 to chamber 22.

It will be appreciated by those skilled in the art that neither insert 24, nor radiation opaque membrane 10, nor the non-migrated cells adhered to it, need be removed prior to measuring the radiation corresponding to the migrated cells. This permits repeated measurements of the chemotactic response of the same cell sample, thus permitting simple and rapid quantitative determinations in a kinetic, or time-dependent, profile of the chemotactic response with a minimum number of test samples. In addition, the devices used to measure the radiation, such as plate readers or spectrophotometers, are highly sensitive and accurate pieces of equipment and provide objective data corresponding to the number of migrated cells. This is a distinct advantage over the prior art procedures which rely upon subjective physical examination under a microscope.

As mentioned above, the chemotaxis assay of this invention can be used with a variety of cell types. Examples include, but are not limited to, macrophages, eosinophils, fibroblasts, endothelial cells, epithelial cells, PMN's, tumor cells and prokaryotic organisms. The only practical limitations on the cell type are its ability to exhibit a chemotactic response and its ability to be labeled.

In accordance with the present invention, the cell sample is labeled with a fluorescent dye. The process of labeling cells with dyes is well known, as is the variety of fluorescent dyes that may be used for labeling particular cell types. See e.g. R. Haugland, Handbook of Fluorescent Probes and Research Chemicals, Molecular Probes, Inc. (1989). A particularly preferred fluorescent dye for use with an HL-60 cell line (ATCC No. CCL 240) in the present invention is Di-I (Molecular Probes, Inc.; Eugene, OR).

It should be mentioned here that, in theory, non-fluorescent dyes may be used in the present invention. At the present time however, there are no known devices that can be used to measure the transmitted light from migrated cells to the exclusion of the transmitted light from the non-migrated cells. Accordingly, the practical utility of using non-fluorescent dyes in the present invention awaits the discovery or invention of such a device.

A particularly novel aspect of the present invention is the use of a radiation opaque membrane which is not substantially transmissive to at least the wavelength of electromagnetic radiation used to stimulate the labeled cells or the wavelength of electromagnetic radiation emitted by the labeled cells. Preferably, the radiation opaque membrane is not substantially transmissive to both wavelengths of electromagnetic radiation, which would protect against excitation of non-migrated cells and would also prevent transmission of radiation emitted by any non-migrated cells that may, nevertheless, become stimulated. It may be advantageous in certain situations, such as for example where mixed cell types and multiple labeling dyes are used, to selectively block either the excitation wavelength or the emission Wavelength. Because the radiation opaque membrane is porous, it will be impossible to completely block all transmission of radiation across the radiation opaque membrane, simply because some radiation will be transmitted through the pores in the radiation opaque membrane. In practice, however, the quantum of radiation so transmitted will be relatively constant and negligible in terms of the quantum of radiation radiating from the migrated cells. Generally speaking, however, the radiation opaque membrane (absent any pores) should have a blocking efficiency of at least approximately 95%. That is, the membrane should be capable of blocking at least approximately 95% of the intended radiation, either the radiation used to stimulate the cells, the radiation emitted by the labeled cells, or the combined stimulation and emission radiation.

In accordance with the present invention, such membranes permit the measurement of radiation emitted from the labeled cells that have migrated through the radiation opaque membrane without interference from radiation emitted from the labeled cells that have not migrated, without the need to remove the non-migrated cells from the radiation opaque membrane. This is a significant advantage of the present invention over the prior art procedures, not only because it avoids the tedious steps of removing the filter and scraping the non-migrated cells from the filter, but also because it is non-destructive of the cell sample and thus permits repeated measurements of the same test sample at different time intervals.

The radiation opaque membrane itself may be of any convenient construction, so long as it has the properties mentioned above. In general, the radiation opaque membrane 10 comprises a non-fibrous film 12 of polyester, polycarbonate, polyethylene terephthalate, polylactic acid, nylon, etc. Depending on the type of film used, the film may be dyed to obtain the radiation blocking properties discussed above. In lieu of or in addition to using a dyed film, one or more radiation blocking layers 14 may be applied to the film by any conventional process suitable for the particular film and blocking layer(s) being used, such as coating under vacuum, layer transfer, sputtering, spin coating, vacuum deposition, etc. The thickness of the radiation opaque membrane 10 is not critical to the invention. Membranes having a thickness in the range customarily used in the art are suitable for use herein.

As already noted, the radiation opaque membrane must have a plurality of pores 16 disposed substantially perpendicular to the plane of the radiation opaque membrane to permit the migration of cells across the radiation opaque membrane. The diameter of the pores is not particularly critical and, to a large extent, depends upon the size of the cells being studied. Generally speaking, the pores 16 must be of such diameter to prevent the cells from passively traversing the radiation opaque membrane while at the same permitting the cells to actively "crawl" through the radiation opaque membrane. It is readily within the skill of the ordinary artisan to determine the appropriate pore size for a particular chemotaxis assay without undue experimentation. Pores of suitable size can be provided in the film by any known process, such as atomic etching. If a radiation blocking layer(s) is to be applied to the film, it may be done either before or after the pores have been provided.

EXAMPLES

Cell Sample

The cell line HL-60 (ATCC No. CCL 240) was maintained in logarithmic growth phase as a suspension culture at about $10^6$ cells/mL. in RPMI 1640 medium (Mediatech Cellgrow, Fisher Scientific, Pittsburgh, PA.) supplemented with 20% (volume by volume) fetal bovine serum. (Hyclone Laboratories, Salt Lake City, UT). The cells were differentiated into mature myelocytes and neutrophils by incubating the cells for 48 hours at 37° C. in media containing 1.5% (volume by volume) dimethylsulfoxide.

Cell Labeling

Following the treatment with dimethylsulfoxide, the cells were incubated with 50 μM Di-I fluorescent dye (Molecular Probes, Inc., Eugene, OR) at room temperature for 0.5–2 hours. The cells were then washed with Hanks' Balanced Salt Solution ("HBSS") (Sigma Chemical Co., St. Louis, MO.) and re-suspended in HBSS to achieve a cell concentration of $10^6$ cells/mL. The fluorescence of 0.5 mL. of cell suspension was measured in a Cytofluor™ 2300 fluorescent plate reader (Millipore Corp., Marlborough, MA.).

Membrane Preparation

Membrane 1: Polycarbonate film having a plurality of pores of 8 μm diameter were coated with four molecular layers of carbon and one layer of an admixture of gold and palladium in a vacuum evaporator. The resulting radiation opaque membrane had a thickness of about 10 μm and was approximately 97% efficient in blocking the combined stimulation and emission radiation. 6 mm disks of the radiation opaque membrane were glued to the bottom of inserts similar to the Millicell HA-12 mm (Millipore Corp.) or the Transwell-6.5 mm (Costar Corp., Cambridge, MA.) inserts with clear silicone rubber cement.

Membrane 2: A non-porous polyester film(18 μm thick) containing a blue dye (Aquired Technology Inc., Alpharetta, GA.) was subjected to atomic etching to produce a 10 μm thick radiation opaque membrane containing a plurality of pores of 8 μm diameter having a combined radiation blocking efficiency of approximately 99%. 6 mm disks of the radiation opaque membrane were glued to the bottoms of inserts as with membrane 1.

Test Procedure

Figure 5:
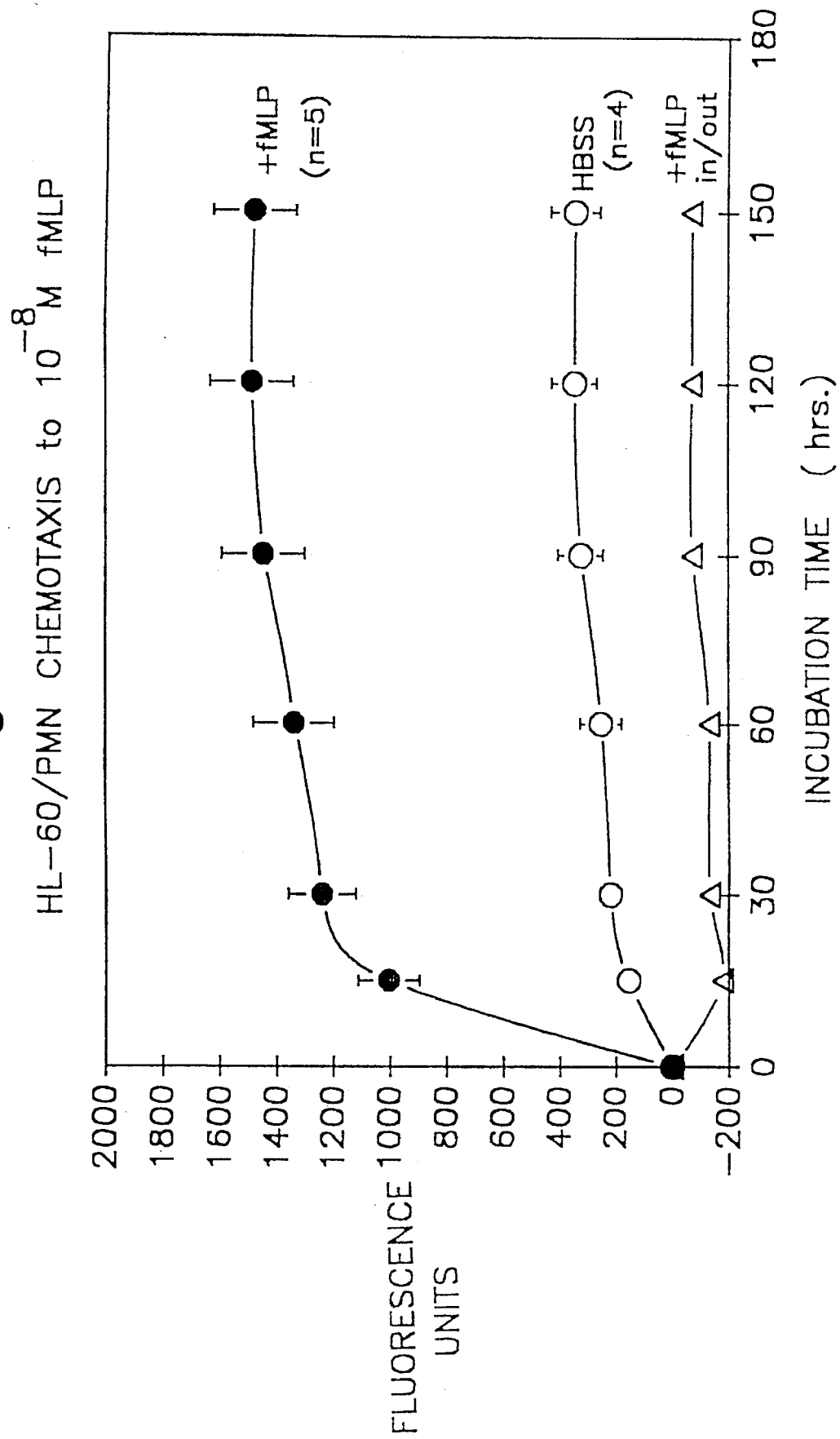

Each insert equipped with the either membrane 1 or membrane 2 were placed in a well of a 24-well culture plate (Falcon, Fisher Scientific). 0.5 mL of labeled cell suspension was placed inside each insert. The plate was incubated for 30 minutes at 37° C. to allow the cells to settle on the radiation opaque membrane. The fluorescence of each well was then measured with the Cytofluor™ 2300 to obtain a zero time reading. 0.5 mL of either N-formyl methionyl leucyl phenylalanine ("f-MLP") (Sigma Chemical Co.) or HBBS was then added to each well. The fluorescence in each well was then measured at periodic time intervals using the Cytofluor™ 2300 at sensitivity setting 4. Results using membrane 1 are reported in Tables 1 and 2 and graphically illustrated in FIGS. 4 and 5. Results using membrane 2 are reported in Table 3 and graphically illustrated in FIGS. 6 and 7.

TABLE 1

| Well Number | Test Solutions well/insert | Fluorescence | | | | | |
|---|---|---|---|---|---|---|---|
| | | 0 hr. | 1 hr. | 2 hr. | 3 hr. | 4 hr. | 5 hr. |
| 1 | HBSS/HBSS | 546 | 757 | 862 | 922 | 927 | 904 |
| 2 | HBSS/f-MLP[1] | 383 | 1046 | 1355 | 1433 | 1370 | 1359 |
| 3 | f-MLP[2]/f-MLP | 706 | 654 | 708 | 732 | 728 | 753 |
| 4 | f-MLP[2]/f-MLP | 467 | 412 | 435 | 460 | 447 | 454 |
| 5 | Blank | 130 | 124 | 125 | 125 | 125 | 125 |
| 6 | Blank | 132 | 127 | 127 | 128 | 127 | 126 |
| 7 | Blank | 131 | 127 | 127 | 128 | 127 | 126 |
| 8 | Blank | 128 | 124 | 126 | 125 | 127 | 125 |
| 9 | Blank | 129 | 125 | 126 | 126 | 126 | 125 |
| 10 | Blank | 130 | 127 | 127 | 127 | 128 | 127 |
| 11 | Blank | 135 | 133 | 132 | 132 | 132 | 132 |
| 12 | Blank | 130 | 126 | 125 | 126 | 125 | 125 |
| 13 | Blank | 132 | 128 | 129 | 130 | 129 | 128 |
| 14 | Blank | 134 | 141 | 136 | 139 | 136 | 137 |
| 15 | Blank | 137 | 134 | 133 | 134 | 134 | 132 |
| 16 | Blank | 136 | 131 | 132 | 133 | 132 | 132 |
| 17 | Blank | 135 | 134 | 132 | 134 | 131 | 132 |
| 18 | Blank | 137 | 132 | 131 | 132 | 132 | 133 |
| 19 | Blank | 136 | 132 | 131 | 132 | 132 | 133 |
| 20 | Blank | 139 | 135 | 132 | 135 | 134 | 135 |
| 21 | Blank | 141 | 135 | 136 | 138 | 136 | 137 |
| 22 | Blank | 140 | 137 | 137 | 138 | 136 | 137 |
| 23 | 0.5 mL cells | 9999[3] | 9999 | 9999 | 9999 | 9999 | 9999 |
| 24 | 0.5 mL cells | 9999 | 9999 | 9999 | 9999 | 9999 | 9999 |

Notes:
1. Conc. = $10^{-7}$ M
2 f-MLP added to cell suspension immediately before start of experiment.
3. Fluorescence was greater than measurable at selected sensitivity setting.

TABLE 2

| Well Number | Test Solutions insert/well | FLUORESCENCE | | | | | | |
|---|---|---|---|---|---|---|---|---|
| | | 0 min. | 15 min. | 30 min. | 60 min. | 90 min. | 120 min. | 150 min. |
| 1 | HBSS/f-MLP[1] | 2927 | 4195 | 4475 | 4642 | 4761 | 4801 | 4788 |
| 2 | HBSS/f-MLP | 2895 | 4165 | 4400 | 4539 | 4642 | 4681 | 4655 |
| 3 | HBSS/f-MLP | 2631 | 3398 | 3584 | 3645 | 3728 | 3759 | 3728 |
| 4 | HBSS/f-MLP | 2594 | 3446 | 3707 | 3813 | 3932 | 3988 | 3999 |
| 5 | HBSS/f-MLP | 2515 | 3388 | 3594 | 3614 | 3717 | 3759 | 3770 |
| 6 | f-MLP[2]/f-MLP | 2854 | 2675 | 2721 | 2721 | 2783 | 2783 | 2783 |
| 7 | HBSS/HBSS | 2558 | 2683 | 2736 | 2783 | 2862 | 2886 | 2911 |
| 8 | HBSS/HBSS | 2862 | 2977 | 3028 | 3053 | 3114 | 3132 | 3105 |
| 9 | HBSS/HBSS | 3105 | 3194 | 3221 | 3220 | 3294 | 3313 | 3294 |
| 10 | HBSS/HBSS | 2377 | 2660 | 2767 | 2846 | 2927 | 2952 | 2960 |
| 11 | Blank | 165 | 163 | 162 | 163 | 160 | 160 | 160 |
| 12 | Blank | 166 | 163 | 164 | 162 | 161 | 160 | 657 |
| 13 | Blank | 166 | 163 | 163 | 163 | 158 | 161 | 157 |
| 14 | Blank | 166 | 166 | 163 | 163 | 163 | 162 | 159 |
| 15 | Blank | 162 | 160 | 160 | 159 | 156 | 157 | 156 |
| 16 | Blank | 163 | 160 | 159 | 159 | 156 | 157 | 153 |
| 17 | Blank | 162 | 161 | 160 | 159 | 158 | 156 | 156 |
| 18 | Blank | 164 | 161 | 162 | 159 | 158 | 151 | 147 |
| 19 | Blank | 163 | 161 | 162 | 158 | 158 | 158 | 154 |
| 20 | Blank | 162 | 161 | 160 | 159 | 158 | 153 | 145 |
| 21 | Blank | 168 | 166 | 165 | 163 | 163 | 163 | 160 |
| 22 | Blank | 165 | 164 | 163 | 159 | 160 | 151 | 151 |

TABLE 2-continued

| Well Number | Test Solutions insert/well | FLUORESCENCE | | | | | | |
|---|---|---|---|---|---|---|---|---|
| | | 0 min. | 15 min. | 30 min. | 60 min. | 90 min. | 120 min. | 150 min. |
| 23 | Blank | 171 | 168 | 168 | 164 | 150 | 166 | 162 |
| 24 | Blank | 172 | 170 | 169 | 153 | 151 | 162 | 162 |

Notes:
1. Conc. = $10^{-8}$ M
2. f-MLP added to cell suspension immediately before start of experiment

TABLE 3

| Well Number | Test Solutions insert/well | Fluorescence | | | | |
|---|---|---|---|---|---|---|
| | | 0 hr. | 0.5 hr. | 1 hr. | 2 hr. | 3 hr. |
| 1 | HBSS/HBSS[1] | 1079 | 1378 | 1586 | 1770 | 1810 |
| 2 | HBSS/HBSS | 891 | 1058 | 1194 | 1351 | 1421 |
| 3 | HBSS/HBSS | 940 | 1221 | 1382 | 1533 | 1617 |
| 4 | Blank | 178 | 169 | 169 | 167 | 166 |
| 5 | f-MLP[2]/f-MLP | 961 | 1245 | 1390 | 1564 | 1711 |
| 6 | 0.3 mL cells | 9999 | 9999 | 9999 | 9999 | 9999 |
| 7 | HBSS/f-MLP[3] | 1055 | 1770 | 2066 | 2351 | 2536 |
| 8 | HBSS/f-MLP | 1064 | 1454 | 1846 | 2143 | 2292 |
| 9 | HBSS/f-MLP | 1097 | 1775 | 2185 | 2411 | 2432 |
| 10 | Blank | 178 | 187 | 196 | 191 | 190 |
| 11 | f-MLP/f-MLP | 1049 | 1277 | 1413 | 1538 | 1582 |
| 12 | 0.3 mL cells | 9999[4] | 9999 | 9999 | 9999 | 9999 |
| 13 | HBSS/HBSS[5] | 1425 | 1491 | 1577 | 1682 | 1735 |
| 14 | HBSS/HBSS | 1359 | 1454 | 1491 | 1551 | 1645 |
| 15 | HBSS/HBSS | 1340 | 1386 | 1478 | 1582 | 1650 |
| 16 | Blank | 179 | 172 | 176 | 178 | 171 |
| 17 | f-MLP/f-MLP | 1187 | 1181 | 1516 | 1622 | 1673 |
| 18 | 0.4 mL cells | 9999 | 9999 | 9999 | 9999 | 9999 |
| 19 | HBSS/f-MLP | 1277 | 1573 | 1701 | 1836 | 1851 |
| 20 | HBSS/f-MLP[6] | 1228 | 5928 | 6063 | 6342 | 6504 |
| 21 | HBSS/f-MLP | 1242 | 1207 | 1830 | 1931 | 1969 |
| 22 | Blank | 176 | 171 | 169 | 167 | 166 |
| 23 | f-MLP/f-MLP | 1231 | 1325 | 1454 | 1541 | 1604 |
| 24 | 0.4 mL cells | 9999 | 9999 | 9999 | 9999 | 9999 |

Notes:
1. Transwell-type inserts used for wells 1–12.
2. f-MLP added to cell suspension immediately before start of experiment.
3. Conc. = $2 \times 10^{-8}$ M
4. Fluorescence greater than measurable at selected sensitivity setting.
5. Millicell-type inserts used for wells 13–24.
6. Insert leaked

What is claimed is:

1. A non-destructive chemotaxis assay procedure comprising the steps of:
 a) labeling cells with a fluorescent dye;
 b) placing the labeled cells in a first chamber;
 c) placing a chemical agent in a second chamber adjacent to said first chamber, said chemical agent being capable of inducing migration of said labeled cells from said first chamber to said second chamber;
 d) separating said first chamber from said second chamber with a radiation opaque membrane, said radiation opaque membrane having a plurality of substantially perpendicular transverse pores therein;
 e) stimulating the labeled cells on the side of the membrane closest to said second chamber with electromagnetic radiation of a first wavelength whereby said labeled cells will emit electromagnetic radiation of a second wavelength; and
 f) measuring the emitted electromagnetic radiation from the side of the radiation opaque membrane closest to the second chamber; wherein said radiation opaque membrane comprises a film which is not substantially transmissive to at least one of said first and second wavelengths of electromagnetic radiation.

2. The procedure of claim 1, wherein the fluorescent dye is Di-I.

3. The procedure of claim 3, wherein the radiation opaque membrane comprises a polyester film containing a blue dye.

4. The procedure of claim 1, wherein the radiation opaque membrane comprises a polycarbonate film coated with four layers of carbon and one layer of an admixture of gold and palladium.

5. The procedure of claim 1, wherein step (f) comprises measuring the electromagnetic radiation with a fluorescent plate reader.

6. The procedure of claim 1, further comprising the step of repeating steps (e) and (f) at least once at a predetermined time interval.

7. The procedure of claim 6, wherein the dye comprises a fluorescent dye.

8. The procedure of claim 7, wherein the fluorescent dye is Di-I.

9. The procedure of claim 8, wherein the radiation opaque membrane comprises a polyester film containing a blue dye.

10. The procedure of claim 8, wherein the radiation opaque membrane comprises a polycarbonate film coated with four layers of molecular carbon and one layer of an admixture of gold and palladium.

11. The procedure of claim 7, wherein the step (f) comprises measuring the electromagnetic radiation with a fluorescent plate reader.

12. The procedure of claim 6, wherein the film has a radiation blocking efficiency of at least approximately 95%.

13. The procedure of claim 1, wherein the film has a radiation blocking efficiency of at least approximately 95%.

14. The procedure of claim 13, wherein the film has a radiation blocking efficiency of at least approximately 97%.

15. A chemotaxis assay procedure comprising measuring the migration of cells across a radiation opaque membrane, wherein said procedure is non-destructive of said cells.

* * * * *